(12) United States Patent
Samuels et al.

(10) Patent No.: US 11,471,504 B2
(45) Date of Patent: Oct. 18, 2022

(54) COMBINATION THERAPY FOR THE TREATMENT OF CANCER

(71) Applicant: Yeda Research and Development Co. Ltd., Rehovot (IL)

(72) Inventors: Yardena Samuels, Rehovot (IL); Rand Arafeh, Rehovot (IL); Karen Flores, Rehovot (IL); Rony Seger, Rehovot (IL); Ehud Wainstein, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 114 days.

(21) Appl. No.: 16/633,175

(22) PCT Filed: Jul. 24, 2018

(86) PCT No.: PCT/IL2018/050824
§ 371 (c)(1),
(2) Date: Jan. 23, 2020

(87) PCT Pub. No.: WO2019/021284
PCT Pub. Date: Jan. 31, 2019

(65) Prior Publication Data
US 2021/0154261 A1 May 27, 2021

(30) Foreign Application Priority Data
Jul. 24, 2017 (IL) .......................................... 253642

(51) Int. Cl.
*A61K 38/10* (2006.01)
*A61P 35/00* (2006.01)
*A61K 31/4184* (2006.01)
*A61K 31/519* (2006.01)

(52) U.S. Cl.
CPC .......... *A61K 38/10* (2013.01); *A61K 31/4184* (2013.01); *A61K 31/519* (2013.01); *A61P 35/00* (2018.01)

(58) Field of Classification Search
None
See application file for complete search history.

(56) References Cited

U.S. PATENT DOCUMENTS 9,695,402 B2 * 7/2017 Seger .................... C12Y 207/11
2016/0340655 A1 11/2016 Seger et al.

FOREIGN PATENT DOCUMENTS

WO WO 2008/104979 9/2008
WO WO 2015/040609 3/2015
WO WO 2019/021284 1/2019

OTHER PUBLICATIONS

Plotnikov et al. "The nuclear translocation of ERK1/2 as an anti-cancer target," Nat. Commun. 6:6685 doi: 10.1038/ncomms7685 (2015) (Year: 2015).*
Lugowska et al. "Trametinib: a MEK inhibitor for management of metastatic melanoma," OncoTargets and Therapy 2015:8 2251-2259 (Year: 2015).*
International Preliminary Report on Patentability dated Feb. 6, 2020 From the International Bureau of WIPO Re. Application No. PCT/IL2018/050824. (9 Pages).
International Search Report and the Written Opinion dated Oct. 30, 2018 From the International Searching Authority Re. Application No. PCT/IL2018/050824. (17 Pages).
Office Action and Search Report dated May 10, 2018 From the Israel Patent Office Re. Application No. 253642. (9 Pages).
Arafeh et al. "Combined Inhibition of MEK and Nuclear ERK Translocation has Synergistic Antitumor Activity in Melanoma Cells", Scientific Reports, XP055516634, 7(1): 16345, pp. 1-9, Nov. 27, 2017 Abstract, p. 1, Para [0001], p. 7, Para [0010].
Asati et al. "PI3K/Akt/mTOR and Ras/Raf/MEK/ERK Signaling Pathways Inhibitors as Anticancer Agents: Structural and Pharmacological Perspectives", European Journal of Medicinal Chemistry, 109: 314-341, Available Online Jan. 12, 2016.
Dummer et al. "Binimetinib Versus Dacarbazine in Patients With Advanced NRAS-Mutant Melanoma (NEMO): A Multicentre, Open-Label, Randomised, Phase 3 Trial", The Lancet Oncology, 18(4): 435-445, Pubhshed Online Mar. 8, 2017. p. 439, Left col. Second Full Para—p. 440, Left col. First Para, p. 444, Left col. Second Full Para, Tables 1, 2.
Inman "Dabrafenib/Trametinib Combination Approved for Advanced Melanoma", Retrieved From the Internet, Onclive.com, p. 1-3, Jan. 9, 2014.
Nissan et al. "Loss of NF1 in Cutaneous Melanoma Is Associated With RAS Activation and MEK Dependence", Cancer Research, 74(8): 2340-2350, Published Online Feb. 27, 2014. Abstract, p. 2341, First Para, p. 2348, Last Para.
Plotnikov et al. "The Nuclear Translocation of ERK1/2 as an Anticancer Target", Nature Communications, XP055331433, 6: 6685, pp. 1-11, Mar. 30, 2015. Abstract, p. 2, left-hand col. Para [0001]—p. 10, right-hand col. Para [0003].
Wainstein et al. "The Dynamic Subcellular Localization of ERK: Mechanisms of Translocation and Role in Various Organelles", Current Opinion in Cell Biology, XP029497505, 39: 15-20, Jan. 29, 2016 Abstract, p. 15, left-hand col. Para [0001]—p. 18, right-hand col. Para [0001].

\* cited by examiner

*Primary Examiner* — Christina Bradley

(57) ABSTRACT

An article of manufacture is disclosed which comprises:
(i) a peptide agent which is capable of preventing extracellular signal-regulated kinase1/2 (ERK) translocation into the nucleus; and
(ii) a MEK inhibitor.
Uses thereof are also disclosed.

6 Claims, 6 Drawing Sheets
Specification includes a Sequence Listing.

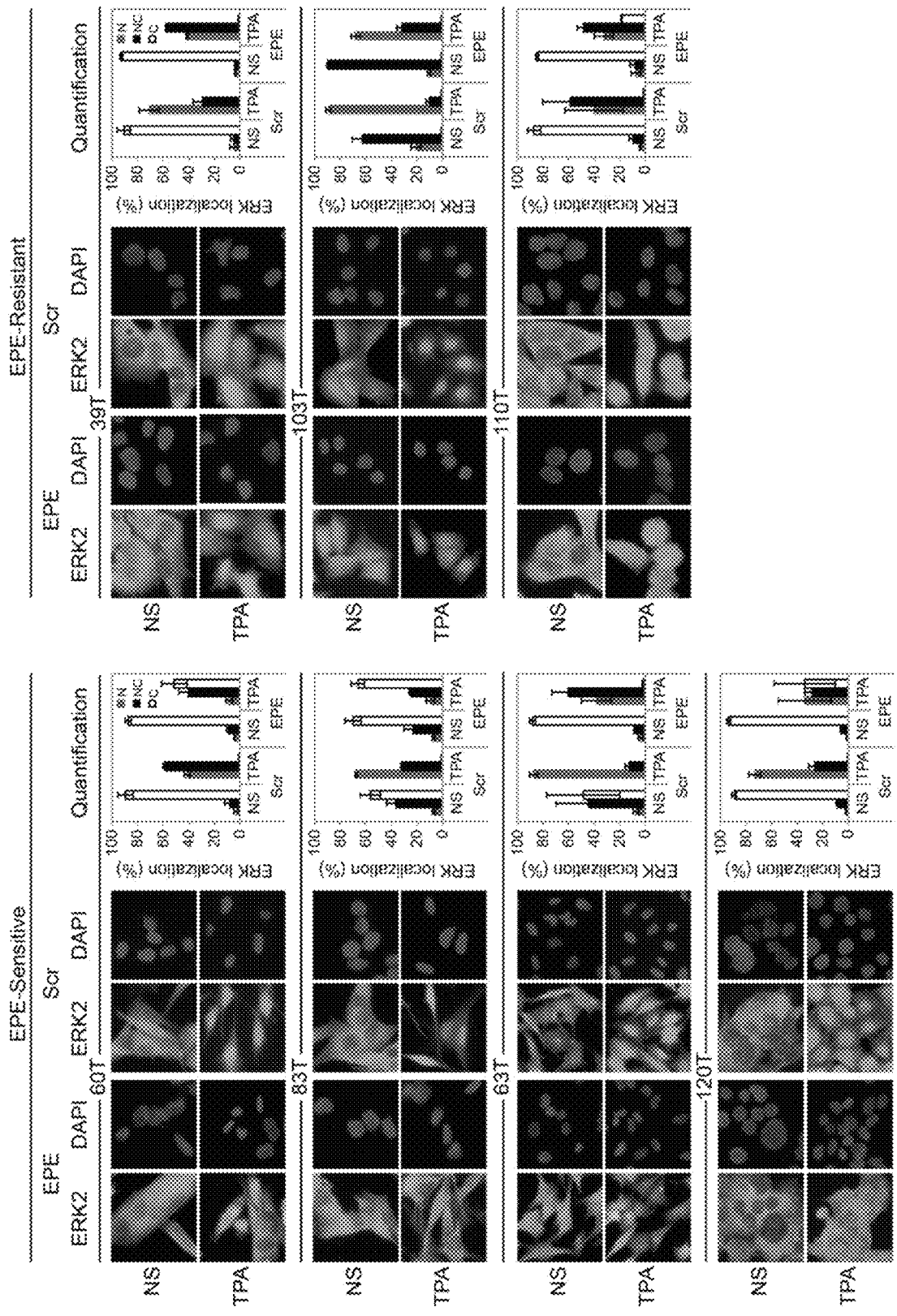

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial Sequence
<220> FEATURE:
<223> OTHER INFORMATION: Scrambled peptide sequence
<220> FEATURE:
<221> NAME/KEY: MISC_FEATURE
<222> LOCATION: (1)..(1)
<223> OTHER INFORMATION: N-terminal conjugated to myristic acid
<220> FEATURE:
<221> NAME/KEY: MISC_FEATURE
<222> LOCATION: (18)..(18)
<223> OTHER INFORMATION: C-terminal amidated

<400> SEQUENCE: 1

Gly Asn Ile Leu Ser Gln Glu Leu Pro His Ser Gly Asp Leu Gln Ile
1               5                   10                  15

Gly Leu

<210> SEQ ID NO 2
<211> LENGTH: 18
<212> TYPE: PRT
<213> ORGANISM: Artificial Sequence
<220> FEATURE:
<223> OTHER INFORMATION: EPE peptide sequence
<220> FEATURE:
<221> NAME/KEY: MISC_FEATURE
<222> LOCATION: (1)..(1)
<223> OTHER INFORMATION: N-terminal conjugated to myristic acid
<220> FEATURE:
<221> NAME/KEY: MISC_FEATURE
<222> LOCATION: (18)..(18)
<223> OTHER INFORMATION: C-terminal amidated

<400> SEQUENCE: 2
```

```
Gly Gln Leu Asn His Ile Leu Gly Ile Leu Gly Glu Pro Glu Gln Glu
1               5                   10                  15

Asp Leu

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Gly Gln Leu Asn His Ile Leu Gly Ile Leu Gly Glu Pro Glu Gln Glu
1               5                   10                  15

Asp

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 4

Gly Gln Leu Asn His Ile Leu Gly Ile Leu Gly Xaa Pro Xaa Gln Glu
1               5                   10                  15

Asp Leu

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 5

Gln Leu Asn His Ile Leu Gly Ile Leu Gly Xaa Pro Xaa Gln Glu Asp
1               5                   10                  15

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide

<400> SEQUENCE: 6

Leu Asp Gln Leu Asn His Ile Leu Gly Ile Leu Gly Glu Pro Glu Gln
1               5                   10                  15

Glu Asp
```

```
<210> SEQ ID NO 7
<211> LENGTH: 17
<212> TYPE: PRT
<213> ORGANISM: Artificial Sequence
<220> FEATURE:
<223> OTHER INFORMATION: Synthetic peptide

<400> SEQUENCE: 7

Gly Gln Leu Asn His Ile Leu Gly Ile Leu Gly Asp Pro Asp Gln Glu
1               5                   10                  15

Asp

<210> SEQ ID NO 8
<211> LENGTH: 7
<212> TYPE: PRT
<213> ORGANISM: Artificial Sequence
<220> FEATURE:
<223> OTHER INFORMATION: example of cell penetrating peptide (CPP) amino
      acid sequences

<400> SEQUENCE: 8

Tyr Gly Arg Lys Lys Arg Arg
1               5

<210> SEQ ID NO 9
<211> LENGTH: 11
<212> TYPE: PRT
<213> ORGANISM: Artificial Sequence
<220> FEATURE:
<223> OTHER INFORMATION: example of cell penetrating peptide (CPP) amino
      acid sequences

<400> SEQUENCE: 9

Tyr Gly Arg Lys Lys Arg Arg Gln Arg Arg Arg
1               5                   10

<210> SEQ ID NO 10
<211> LENGTH: 5
<212> TYPE: PRT
<213> ORGANISM: Artificial Sequence
<220> FEATURE:
<223> OTHER INFORMATION: example of cell penetrating peptide (CPP) amino
      acid sequences

<400> SEQUENCE: 10

Arg Arg Gln Arg Arg
1               5

<210> SEQ ID NO 11
<211> LENGTH: 11
<212> TYPE: PRT
<213> ORGANISM: Artificial Sequence
<220> FEATURE:
<223> OTHER INFORMATION: example of cell penetrating peptide (CPP) amino
      acid sequences

<400> SEQUENCE: 11

Tyr Ala Arg Ala Ala Ala Arg Gln Ala Arg Ala
1               5                   10

<210> SEQ ID NO 12
<211> LENGTH: 3
<212> TYPE: PRT
<213> ORGANISM: Artificial Sequence
<220> FEATURE:
<223> OTHER INFORMATION: Synthetic peptide
```

```
-continued

<220> FEATURE:
<221> NAME/KEY: MISC_FEATURE
<222> LOCATION: (1)..()
<223> OTHER INFORMATION: X is selected from the group consisting of
      serine, phosphoserine, threonine, phosphothreonine, aspartic acid
      and glutamic acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: X is proline
<220> FEATURE:
<221> NAME/KEY: MISC_FEATURE
<222> LOCATION: (3)..(3)
<223> OTHER INFORMATION: X is selected from the group consisting of
      serine, phosphoserine, threonine, phosphothreonine, aspartic acid
      and glutamic acid

<400> SEQUENCE: 12

Xaa Xaa Xaa
1
```

COMBINATION THERAPY FOR THE TREATMENT OF CANCER

FIELD AND BACKGROUND OF THE INVENTION

The present invention, in some embodiments thereof, relates to methods of treating cancer and, more particularly, but not exclusively, to treating melanoma including BRAF mutant melanoma, NRAS mutant melanoma and NF1 mutant melanoma.

Malignant melanoma is the most fatal type of skin cancer. The incidence of melanoma continues to increase, and represents a significant health problem worldwide. Over the past decade, comprehensive sequencing efforts that shed light into the melanoma genetic landscape have enabled the discovery of several novel driver genes. Melanomas are divided into four different subgroups depending on their driving mutation's status. The first group include BRAF (most often BRAF$V^{600E}$) mutant melanomas (~50%), the second group are NRAS$^{Q61L/R}$ mutant melanomas (15-20%), the third group are NF1 mutant melanomas (15%), and the fourth group are triple wild-type melanomas (15-20%). The driving mutations of the first three subgroups are all known to hyperactivate the ERK cascade, making it a favorable potential candidate for targeted therapy, considering ERK1/2 itself as a very good node for effective interruption of ERK signaling.

The identification of these mutations motivated the development of targeted drugs against different tiers of the ERK cascade. Efforts to develop RAS inhibitors have mostly failed, with no targeted therapy against this protein so far. However, inhibitors of BRAF, MEK1/2 and recently also ERK1/2, have been developed in the past years. Although the initial response rate to Vemurafenib is more than 70% of the mutated BRAF melanoma, with significant survival benefit, tumor resistance occurs within 2-18 months of treatment. Although MEK mutations in melanoma occur rarely (~1%), its activity is elevated in almost all melanomas. Recent efforts have led to the development of the MEK inhibitor Trametinib. In phase II clinical trials, trametinib treatment showed significant clinical benefit in BRAF melanoma patients who had not been previously treated with a BRAF inhibitor, and minimal activity in sequential therapy in patients previously treated with BRAF inhibitors. These trials initiated a new therapeutic strategy of combining RAF and MEK inhibitors. Indeed, the combination of dabrafenib and trametinib improved anti-tumor activity and survival in BRAF mutant melanoma patients. Concurrently, immunotherapy has transitioned from cytokine-based treatment to antibody-mediated blockade of the cytotoxic T-lymphocyte-associated antigen-4 (CTLA-4) and the programmed cell-death protein 1 (PD-1) immune checkpoints. These changes in the treatment landscape have dramatically improved patient outcomes, with the median overall survival of patients with advanced-stage melanoma increasing from approximately 9 months before 2011 to at least 2 years and probably longer for those with BRAF$^{V600}$ mutant disease.

Although oncogenic mutations in ERK1/2 are extremely rare, its activity is elevated in about 85% of all cancers. Therefore, it is still an attractive therapeutic target due to its central role in integrating signaling from various upstream components. A recently developed ERK1/2 inhibitor SCH772984 showed benefits in reducing tumor growth in BRAF and MEK inhibitor-resistant models. Although inhibition of ERK1/2 mostly reduced cell growth of BRAF mutant melanomas, it also showed some partial reduction in NRAS and KRAS mutant cancer cell growth. Several other ERK1/2 inhibitors are under development, but none of these compounds have been approved for clinical use. Moreover, these inhibitors were proven beneficial almost only in BRAF mutant melanomas, and thus a considerable number of melanoma patients remain without a targetable mutation. Moreover, in patients that do respond to treatment, the heterogeneous nature of melanoma tumors leads to the rapid emergence of resistance, due to escape mechanisms from the inhibitor's blockade, allowing cancer progression. Multiple mechanisms of resistance of BRAF mutant melanomas have been described, which can be classified as intrinsic or acquired. These two types of drug resistance have been shown to result in either reactivation of the ERK1/2 signaling, failure to effectively deactivate ERK1/2, or activate alternative signaling pathways that overcome the inhibition of ERK1/2.

It was previously shown that the nuclear activity of ERK is mainly associated with cell proliferation, whereas ERK negative feedback targets are mostly cytosolic. Therefore, inhibition of nuclear ERK translocation, which reduces nuclear phosphorylaton without affecting much negative feedback loops, should result in inhibition of tumor growth with less or delayed resistance. In a previous study, it was shown that stimulated nuclear translocation of ERK1/2, which is one of the hallmarks of the cascade, is mediated by phosphorylation of ERK's Nuclear Translocation Signal (NTS) that consequently induces binding with importin7 that escorts active ERK1/2 into the nucleus. It was later shown that by using a myristoylated NTS-derived phosphomimetic peptide (EPE peptide), the interaction of Importin7 with ERK1/2, and consequently the nuclear translocation of the latter, are inhibited (WO2008104979).

WO2015040609 teaches that inhibition of ERK1/2 induces apoptosis of BRAF mutant melanoma cells and inhibits the proliferation/survival of many other cancer cells, including BRAF and MEK resistant melanoma cells, but has no effect on the viability of several immortalized cells.

SUMMARY OF THE INVENTION

According to an aspect of some embodiments of the present invention there is provided an article of manufacture comprising:

(i) a peptide agent which is capable of preventing extracellular signal-regulated kinase1/2 (ERK) translocation into the nucleus; and (ii) a MEK inhibitor.

According to an aspect of some embodiments of the present invention there is provided a pharmaceutical composition comprising as active agents:

(i) an agent which is capable of preventing extracellular signal-regulated kinase1/2 (ERK) translocation into the nucleus and;

(ii) a MEK inhibitor;

and a pharmaceutically acceptable carrier.

According to some embodiments of the invention, the article of manufacture or pharmaceutical composition of claims 1 or 2, wherein the MEK inhibitor is selected from the group consisting of trametinib, selumetinib and MEK162.

According to some embodiments of the invention, the article of manufacture or pharmaceutical composition of claim 1, wherein the peptide agent comprises the sequence $X_1X_2X_3$ wherein:

(i) $X_1$ and $X_3$ are each independently selected from the group consisting of serine, phosphoserine, threonine, phosphothreonine, aspartic acid and glutamic acid;

(ii) $X_2$ is proline; and (iii) the peptide is no longer than 30 amino acids.

According to some embodiments of the invention, peptide is no longer than 20 amino acids.

According to some embodiments of the invention, the peptide comprises the sequences as set forth in SEQ ID NO: 2, (GQLNHILGILGEPEQEDL), SEQ ID NO: 3 (GQLN-HILGILGEPEQED) or SEQ ID NO: 6 (LDQLN-HILGILGEPEQED).

According to some embodiments of the invention, the peptide comprises a cell penetrating agent.

According to some embodiments of the invention, the cell penetrating agent comprises myristic acid.

According to some embodiments of the invention, the cell penetrating agent is a cell penetrating peptide.

According to some embodiments of the invention, the article of manufacture or pharmaceutical composition is for use in treating cancer.

According to an aspect of some embodiments of the present invention there is provided an article of manufacture for use in treating a cancer which has not been previously treated with an ERK pathway inhibitor, wherein the article of manufacture comprises:

(i) an agent which is capable of preventing extracellular signal-regulated kinase1/2 (ERK) translocation into the nucleus; and (ii) an ERK pathway inhibitor.

According to some embodiments of the invention, the ERK pathway inhibitor is a BRAF inhibitor.

According to some embodiments of the invention, the BRAF inhibitor is selected from the group consisting of LGX818, Vemurafenib Dabrafenib and Sorafenib.

According to some embodiments of the invention, the ERK pathway inhibitor is a MEK inhibitor.

According to some embodiments of the invention, the MEK inhibitor is selected from the group consisting of trametinib, selumetinib and MEK162.

According to some embodiments of the invention, the cancer is pancreatic cancer or melanoma.

According to some embodiments of the invention, the melanoma is a BRAF mutant melanoma, a NRAS mutant melanoma or a NF1 mutant melanoma.

According to some embodiments of the invention, the NRAS mutant melanoma comprises at least one mutation selected from the group consisting of 63T, 83T, 120T and 60T.

According to some embodiments of the invention, the NF1 mutant melanoma comprises at least one mutation set forth in Table 3.

According to an aspect of some embodiments of the present invention there is provided a peptide for use in treating an NRAS mutant melanoma and an NF1 mutant melanoma, which comprises the sequence $X_1X_2X_3$ wherein:

(i) $X_1$ and $X_3$ are each independently selected from the group consisting of serine, phosphoserine, threonine, phosphothreonine, aspartic acid and glutamic acid;

(ii) $X_2$ is proline; and (iii) the peptide is no longer than 30 amino acids.

According to some embodiments of the invention, the peptide is no longer than 20 amino acids.

According to some embodiments of the invention, the peptide comprises the sequences as set forth in SEQ ID NO: 2, (GQLNHILGILGEPEQEDL), SEQ ID NO: 3 (GQLN-HILGILGEPEQED) or SEQ ID NO: 6 (LDQLN-HILGILGEPEQED).

According to some embodiments of the invention, the peptide comprises a cell penetrating agent.

According to some embodiments of the invention, the cell penetrating agent comprises myristic acid.

According to some embodiments of the invention, the cell penetrating agent is a cell penetrating peptide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-B: The EPE peptide blocks the nuclear translocation in "sensitive" NRAS melanomas. The same seven cell lines selected previously, were serum starved (14 h), pre-treated with EPE or Scr peptide (10μ, 2 h), and stimulated with TPA (100 nM, 15 min) or left untreated (NS). Cells were then fixed and stained with αERK2 Abs and DAPI. (A) The EPE peptide significantly reduces the nuclear translocation of ERK1/2 in the sensitive cells. (B) The effect of EPE peptide on the nuclear translocation of ERK1/2 is modest in resistant cells compared to (A). Bars represent average percentage of cells with mostly nuclear (N, red), nuclear and cytosolic (NC, black) or mostly cytosolic (C, white) staining. Error bars represent standard error of 2 or 3 independent experiments. Quantification was done by counting at least three fields with >150 cells.

DESCRIPTION OF SPECIFIC EMBODIMENTS OF THE INVENTION

The present invention, in some embodiments thereof, relates to methods of treating cancer and, more particularly, but not exclusively, to treating melanoma including BRAF mutant melanoma, NRAS mutant melanoma and NF1 mutant melanoma.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The ERK cascade (RAF-MEK-ERK) is a central signaling pathway that plays an integral role in the initiation and regulation of most stimulated cellular processes such as proliferation, survival and differentiation. The cascade is activated upon stimulation of upstream cell surface receptors that further transmit their signals to RAF mainly through Grb2 and SOS that switch on the small inactive GTPase RAS. This activation of RAS enables the recruitment of RAF (mostly B and CRAFs) to the plasma membrane, promoting their homo- or hetero-dimerization and subsequently their activation. Activated RAFs in turn phosphorylate and activate MEK1 and MEK2 (MEK), which further phosphorylate and activate ERK1/2 (ERK). Once activated, ERK phosphorylates many downstream targets in the cytoplasm and in the nucleus. Essentially, hundreds of protein (more than 300) have been identified as ERK cytosolic and nuclear substrates, as well as ERK interacting proteins. Having a crucial regulatory role in cell function, ERK signaling must be precisely regulated and capable of adapting to dynamic environmental changes.

WO2008/104979 and WO2015/040609 describes peptide agents comprising an EPE motif (referred to herein as EPE peptides) that are capable of preventing extracellular signal-regulated kinase1/2 (ERK) translocation into the nucleus. Such agents were shown to be useful for treating BRAF mutant melanomas.

The present inventors now show that such peptide agents not only reduce the growth of BRAF mutant melanomas, but also several NRAS and NF1 mutant melanomas, insensitive to BRAF inhibition. Further comparison between the selected melanoma cells, showed that the EPE peptide indeed reduced the stimulated nuclear translocation in all cell lines.

Figure 3B:
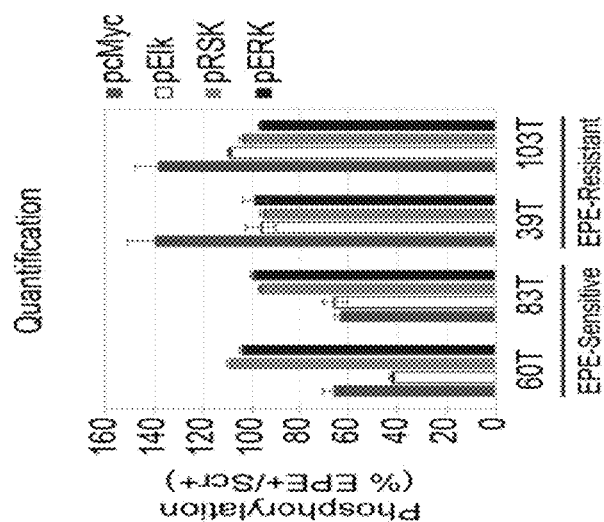
FIGS. 3A-B: The EPE peptide reduces phosphorylation of nuclear targets in NRAS mutant melanomas. Two NRAS melanomas sensitive to EPE peptide (60T an 83T), and two EPE-resistant melanomas (39T and 103T), were serum starved (16 h), pretreated with EPE or Scr peptides (10 µM, 2 h), and stimulated with TPA (100 nM, 15 min) (+) or left untreated (−). Cell lysates where analyzed by WB using the indicated antibodies. (A) (Left) In the EPE-sensitive cells, the peptide reduced the phosphorylation of nuclear targets Elk1 and c-Myc in stimulated and basal state, while not affecting cytosolic target RSK. (Right) In EPE-resistant cells, the peptide had no effect on the phosphorylation of Elk1 and RSK, and slightly increased levels of phospho-c-Myc. (B) Quantification of bands in (A). Bars represent average band density ratio of EPE stimulated samples (EPE+) compared to Scr stimulated samples (Scr+), ±S.E. of 2 or 3 independent experiments. Bands were quantified using ImagJ.
Figure 3A:
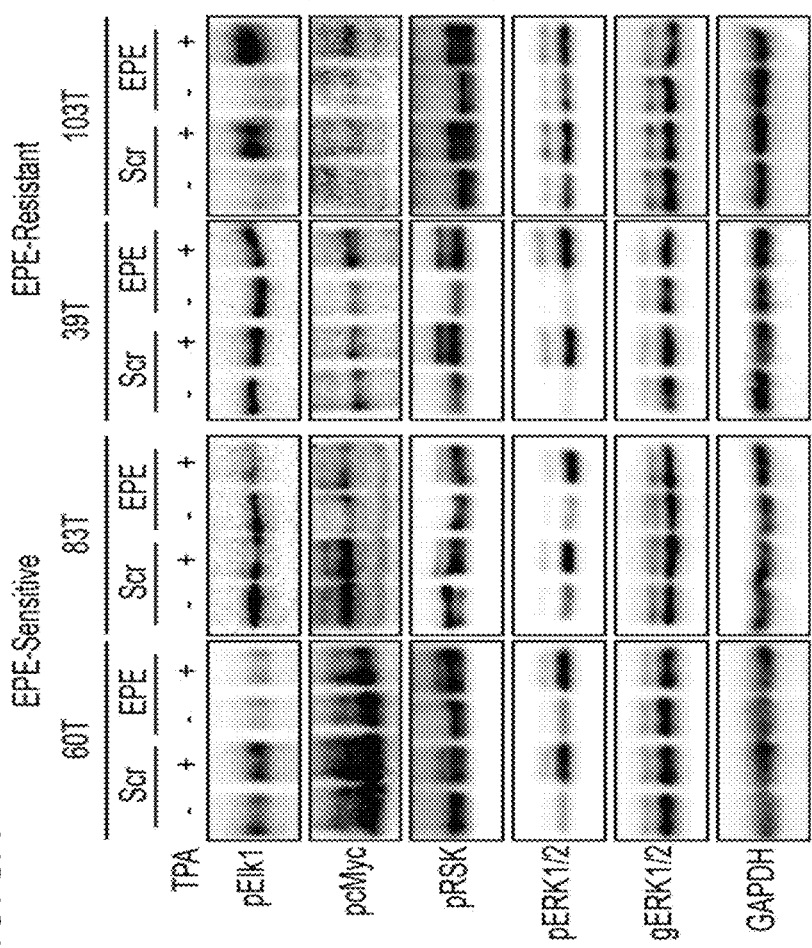

When analyzing the effect of an EPE peptide on ERK cascade signaling, it was found that the EPE peptide significantly downregulated ERK1/2 nuclear targets in EPE-sensitive cells, on both basal and stimulated states. The effect on EPE resistant cells was much smaller and sometimes different, as in the case of Elk1 and c-Myc (FIGS. 3A-B).

Figure 4C:
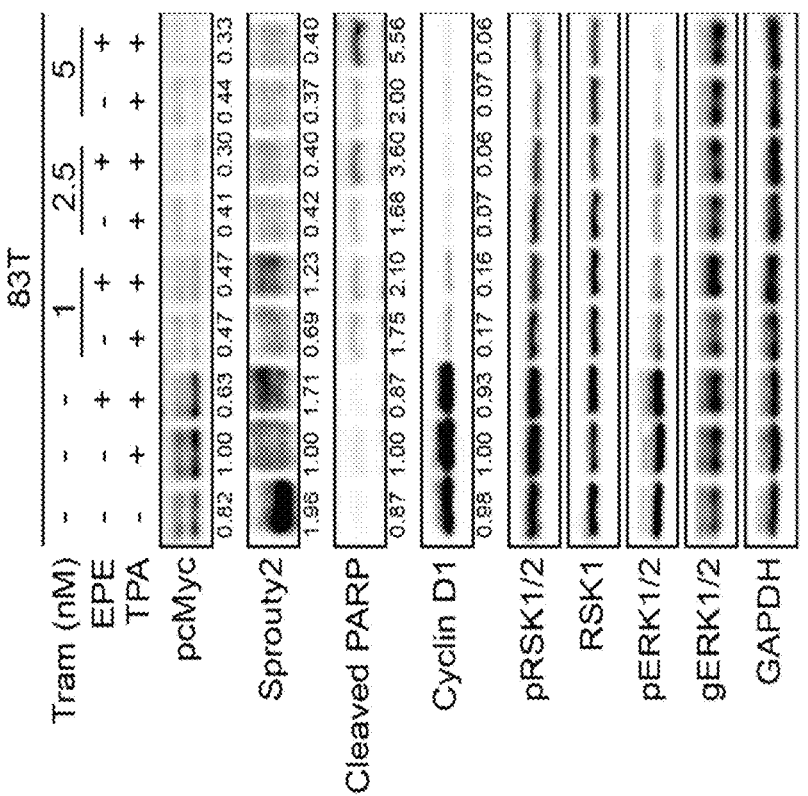
FIGS. 4A-C: Synergistic effect of trametinib and EPE peptide combination in reducing the viability of melanoma cell lines. (A) Synergy between combined treatment of trametinib and EPE peptide in patient-derived melanoma cells. Dose response curves showing growth of melanoma cells treated with combination of trametinib and EPE peptide 10 µM (red), compared to trametinib treatment alone (black). Dots represent triplicates for every concentration point. (B) Effect of the combination of trametinib and EPE peptide on viability of metastatic melanoma cells lines. Cells were treated either with DMSO, trametinib alone (black), EPE peptide alone (10 µM, grey), or trametinib in combination with 10 µM EPE peptide (red) for 72 h. (trametinib concentrations per cell line: 83T and 120T-10 pM; 110T-0.1 nM; 39T-1 nM). Viable cells were quantified using CellTiter-Glo reagent. Bars represent percentage of growth respect to DMSO±S.E. of 2 independent experiments in triplicates, ***$p<0.001$, *$p<0.01$ (Student's t-test) (C) Effect of the combination of trametinib and EPE peptide on ERK1/2 signaling. The combination increases ERK1/2 negative feedback loop mediated by Sprouty2 and apoptosis. NRAS-mutant melanoma cells 83T were serum starved in the presence of trametinib alone (1, 2.5 or 5 nM) or in combination with EPE peptide (10 µM) for 16 hours, and stimulated with TPA 100 nM for 15 min (+) or left untreated (−). Cell lysates where analyzed by WB using the indicated antibodies. Quantified levels are given under the blots. ImageJ was used for the quantification.
Figure 4A:
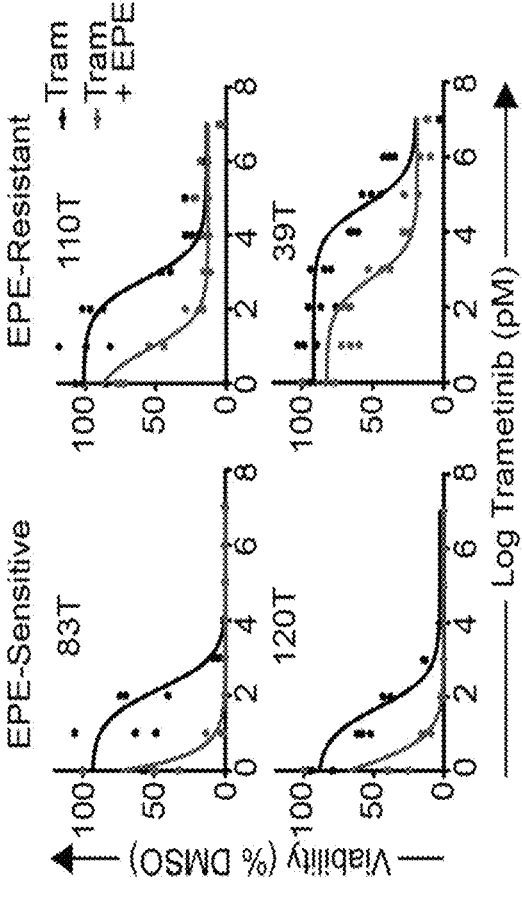
Figure 4B:
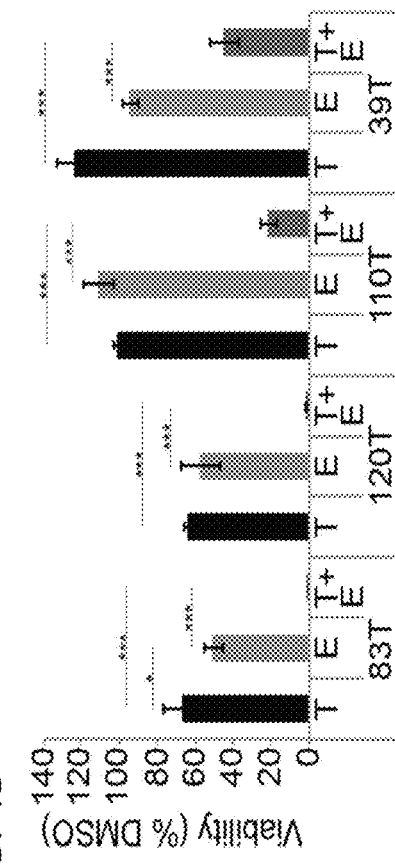

The slight elevation of P-c-Myc prompted the inventors to examine whether the mechanism of resistance to the EPE peptide was due to the ERK cascade itself. Accordingly, the present inventors combined the EPE peptide with the MEK inhibitor trametinib in an attempt to overcome the resistance to the EPE peptide. Surprisingly, the combined inhibition of MEK and ERK nuclear translocation had a synergistic effect, reducing the viability of EPE sensitive NRAS melanomas and the EPE-resistant melanoma cells (FIGS. 4A-C). In EPE-resistant cells, this effect was quite impressive since these cells were also much less sensitive to trametinib alone, but combination of trametinib and EPE peptide completely inhibited their cell growth at concentrations as low as 0.1-1 nM of trametinib. These results confirm that the EPE peptide enters the cells and is able to execute ERK1/2 nuclear translocation inhibitory effects. Moreover, combination of MEK inhibition at very low concentration and ERK1/2 nuclear translocation inhibition, resulted in a more profound decrease in the phosphorylation of ERK1/2's nuclear target c-Myc (FIG. 4C).

The present data confirms the importance of the preservation of the negative feedback loops to overcome drug resistance. It also shows that combination of inhibitors of components of the ERK cascade together with inhibition of the nuclear translocation of ERK1/2, could be an effective treatment for NRAS mutated and other metastatic melanomas.

Figure 6B:
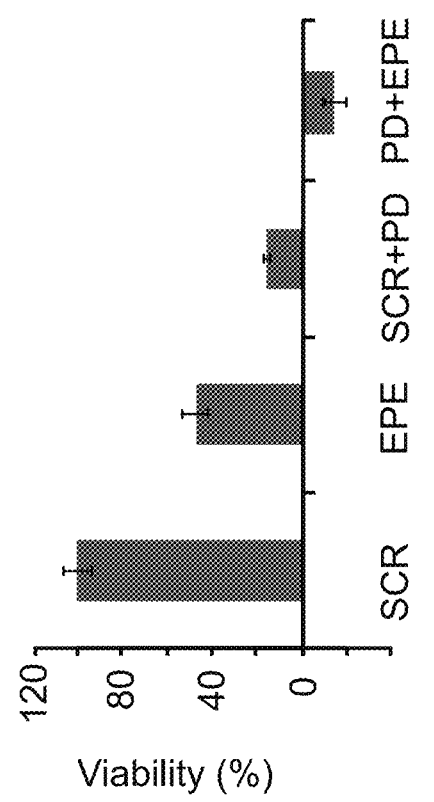
FIGS. 6A-B: Synergistic reduction in pancreatic cancer cell viability under combination treatment of EPE and MEK inhibitor. PD (MEKi) and EPE synergize to reduce cell viability. (A) Panc-1 cells were grown in 1% FCS medium that contained SCR (10 µM), EPE (10 µM), combination of PD (2 µM)+SCR (10 µM), or combination of PD (2 µM)+EPE (10 µM). 72 hours followed seeding, the cells were fixed and viable cells were quantified by methylene blue staining. (B) Aspc-1 cells were grown in 1% FCS medium that contained SCR (10 µM), EPE (10 µM), combination of PD (250 nM)+SCR (10 µM), or Combination of PD (250 nM)+EPE (10 µM). 72 hours followed seeding, the cells were fixed and viable cells were quantified by methylene blue staining.
Figure 6A:
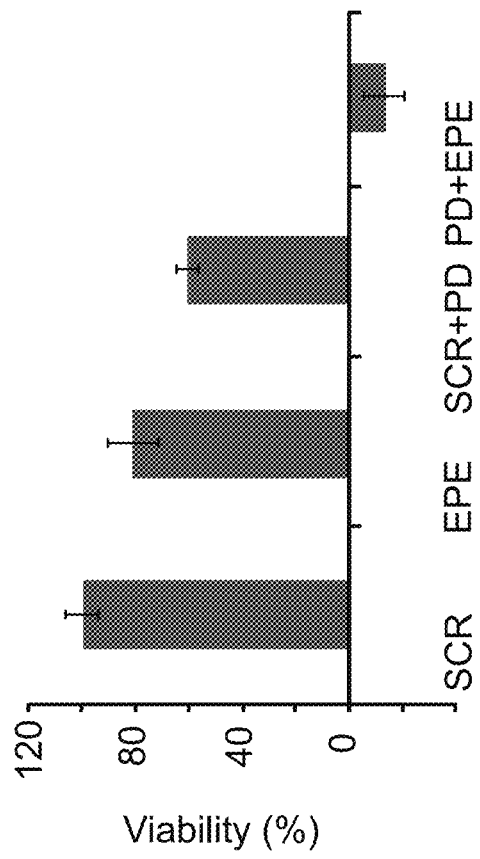

Whilst further reducing the present invention to practice, the present inventors also analyzed the effect of the combination of EPE peptide and trametinib on pancreatic cancer cells and similar to the melanoma cells, showed that the combination had a synergistic effect on cell viability (FIGS. 6A-B).

Taken together, the present inventors propose that the combination of an agent which is capable of preventing extracellular signal-regulated kinase1/2 (ERK) translocation into the nucleus and an ERK pathway inhibitor is effective for treating cancer.

Thus, according to a first aspect of the present invention, there is provided an article of manufacture comprising:

(i) an agent which is capable of preventing extracellular signal-regulated kinase1/2 (ERK) translocation into the nucleus; and (ii) an ERK pathway inhibitor.

Agents which are capable of preventing extracellular signal-regulated kinase1/2 (ERK) translocation into the nucleus include, but are not limited to, inorganic or organic compounds; small molecules (i.e., less than 1000 Daltons) or large molecules (i.e., above 1000 Daltons); biomolecules (e.g. proteinaceous molecules, including, but not limited to, peptides, polypeptide, post-translationally modified protein, antibodies etc.) or a nucleic acid molecule (e.g. double-stranded DNA, single-stranded DNA, double-stranded RNA, single-stranded RNA, or triple helix nucleic acid molecules) or chemicals. The agents may be natural products derived from any known organism (including, but not limited to, animals, plants, bacteria, fungi, protista, or viruses) or from a library of synthetic molecules. The agents can be monomeric as well as polymeric compounds.

According to a particular embodiment, the agent is a peptide.

The phrase "being capable of preventing extracellular signal-regulated kinase1/2 (ERK) translocation into the nucleus" refers to the ability to down-regulate the amount of ERK from translocating from the cytoplasm into the nucleus by at least 10%, 20%, 30%, 40%, 50%, 60%, 70%, 80%, 90% or more. Methods of detecting whether an agent (e.g. a peptide) is capable of preventing ERK translocation are known in the art and for example are described in the Examples section of WO2015/040609, the contents of which are incorporated herein by reference.

The peptide of this aspect of the present invention may be derived from the amino acid sequence of human ERK2 and may be 16, 17, 18, 19, 20, 21, 22, 23, 24, 25, 26, 27, 28, 29 or 30 amino acids long.

According to a particular embodiment, the peptide agent comprises the sequence $X_1X_2X_3$ (SEQ ID NO: 12) wherein:

(i) $X_1$ and $X_3$ are each independently selected from the group consisting of serine, phosphoserine, threonine, phosphothreonine, aspartic acid and glutamic acid;

(ii) $X_2$ is proline; and

Preferably, $X_1$ and $X_3$ are identical—for example both $X_1$ and $X_3$ are glutamic acid.

In one embodiment, the peptide comprises an amino acid sequence which is at least 94% homologous or identical to the sequence as set forth in GQLNHILGILGX$_1$PX$_2$QEDL (SEQ ID NO: 4), 95% homologous or identical to the sequence as set forth in SEQ ID NO: 4, 96% homologous or identical to the sequence as set forth in SEQ ID NO: 4, at least 97% homologous or identical to the sequence as set forth in SEQ ID NO: 4, at least 98% homologous or identical to the sequence as set forth in SEQ ID NO: 4, at least 99% homologous or identical to the sequence as set forth in SEQ ID NO: 4 or 100% homologous or identical to the sequence as set forth in SEQ ID NO: 4 as determined using the Standard protein-protein BLAST [blastp] software of the NCBI.

In another embodiment, the peptide comprises an amino acid sequence which is at least 94% homologous or identical to the sequence as set forth in QLNHILGILGX$_1$PX$_2$QED (SEQ ID NO: 5), 95% homologous or identical to the sequence as set forth in SEQ ID NO: 5, 96% homologous or identical to the sequence as set forth in SEQ ID NO: 5, at least 97% homologous or identical to the sequence as set forth in SEQ ID NO: 5, at least 98% homologous or identical to the sequence as set forth in SEQ ID NO: 5, at least 99% homologous or identical to the sequence as set forth in SEQ ID NO: 5 or 100% homologous or identical to the sequence as set forth in SEQ ID NO: 5 as determined using the Standard protein-protein BLAST [blastp] software of the NCBI.

As mentioned, $X_1$ and $X_2$ in SEQ ID NO: 4 and SEQ ID NO: 5 may be any amino acid (as specified herein below). According to one embodiment, $X_1$ and $X_2$ are each independently selected from the group consisting of glutamic acid, aspartic acid, alanine and serine. For example, the $X_1$ and $X_2$ may both be glutamic acid. For example, the $X_1$ and $X_2$ may both be aspartic acid. For example, the $X_1$ and $X_2$ may both be serine. For example, $X_1$ may be glutamic acid and $X_2$ may be aspartic acid or $X_1$ may be aspartic acid and $X_2$ may be glutamic acid. According to another embodiment, neither $X_1$ nor $X_2$ is alanine.

Thus, according to this aspect of the present invention the peptide is at least 94% homologous or identical to the sequence as set forth in GQLNHILGILGEPEQEDL (SEQ ID NO: 2), 95% homologous or identical to the sequence as set forth in SEQ ID NO: 2, 96% homologous or identical to the sequence as set forth in SEQ ID NO: 2, at least 97% homologous or identical to the sequence as set forth in SEQ ID NO: 2, at least 98% homologous or identical to the sequence as set forth in SEQ ID NO: 2, at least 99% homologous or identical to the sequence as set forth in SEQ ID NO: 2 or 100% homologous or identical to the sequence as set forth in SEQ ID NO: 2 as determined using the Standard protein-protein BLAST [blastp] software of the NCBI, wherein the glutamic acid in position $X_1$ and $X_2$ is not replaceable by another amino acid.

Thus, according to this aspect of the present invention the peptide is at least 94% homologous or identical to the sequence as set forth in GQLNHILGILGEPEQED (SEQ ID NO: 3), 95% homologous or identical to the sequence as set forth in SEQ ID NO: 3, 96% homologous or identical to the sequence as set forth in SEQ ID NO: 3, at least 97% homologous or identical to the sequence as set forth in SEQ ID NO: 3, at least 98% homologous or identical to the sequence as set forth in SEQ ID NO: 3, at least 99% homologous or identical to the sequence as set forth in SEQ ID NO: 3 or 100% homologous or identical to the sequence as set forth in SEQ ID NO: 3 as determined using the Standard protein-protein BLAST [blastp] software of the NCBI, wherein the glutamic acid in position $X_1$ and $X_2$ is not replaceable by another amino acid.

Thus, according to this aspect of the present invention the peptide is at least 94% homologous or identical to the sequence as set forth in LDQLNHILGILGEPEQED (SEQ ID NO: 6), 95% homologous or identical to the sequence as set forth in SEQ ID NO: 6, 96% homologous or identical to the sequence as set forth in SEQ ID NO: 6, at least 97% homologous or identical to the sequence as set forth in SEQ ID NO: 6, at least 98% homologous or identical to the sequence as set forth in SEQ ID NO: 6, at least 99% homologous or identical to the sequence as set forth in SEQ ID NO: 6 or 100% homologous or identical to the sequence as set forth in SEQ ID NO: 6 as determined using the Standard protein-protein BLAST [blastp] software of the NCBI, wherein the glutamic acid in position $X_1$ and $X_2$ is not replaceable by another amino acid.

Thus, according to this aspect of the present invention the peptide is at least 94% homologous or identical to the sequence as set forth in SEQ ID NO: 7 (GQLN-HILGILGDPDQED), 95% homologous or identical to the sequence as set forth in SEQ ID NO: 7, 96% homologous or identical to the sequence as set forth in SEQ ID NO: 7, at least 97% homologous or identical to the sequence as set forth in SEQ ID NO: 7, at least 98% homologous or identical to the sequence as set forth in SEQ ID NO: 7, at least 99% homologous or identical to the sequence as set forth in SEQ ID NO: 7 or 100% homologous or identical to the sequence as set forth in SEQ ID NO: 7 as determined using the Standard protein-protein BLAST [blastp] software of the NCBI, wherein the aspartic acid in position $X_1$ and $X_2$ is not replaceable by another amino acid.

Peptides which are not 100% homologous to the sequences disclosed herein may comprise either conservative or non-conservative substitutions, deletions or additions.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered conservative substitutions.

For producing conservative substitutions by non-naturally occurring amino acids it is also possible to use amino acid analogs (synthetic amino acids) well known in the art. A peptidomimetic of the naturally occurring amino acids is well documented in the literature known to the skilled practitioner.

When effecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall within the scope of the present invention are those which still constitute a polypeptide being able to prevent ERK translocation into the nucleus.

In one embodiment, the peptides of the present invention are typically devoid of the sequence Leu-Aspartic acid.

In another embodiment, the N terminal amino acid of the peptide is glycine.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated amide bonds (—N(CH$_3$)—CO—), ester bonds (—C(=O)—O—), ketomethylene bonds (—CO—CH2—), sulfinylmethylene bonds (—S(=O)—CH2—), α-aza bonds (—NH—N(R)—CO—), wherein R is any alkyl (e.g., methyl), amine bonds (—CH2—NH—), sulfide bonds (—CH2—S—), ethylene bonds (—CH2—CH2—), hydroxyethylene bonds (—CH(OH)—CH2—), thioamide bonds (—CS—NH—), olefinic double bonds (—CH=CH—), fluorinated olefinic double bonds (—CF=CH—), retro amide bonds (—NH—CO—), peptide derivatives (—N(R)—CH2—CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2), which can be used with some embodiments of the invention.

TABLE 1

| One-letter Symbol | Three-Letter Abbreviation | Amino Acid |
|---|---|---|
| A | Ala | Alanine |
| R | Arg | Arginine |
| N | Asn | Asparagine |
| D | Asp | Aspartic acid |
| C | Cys | Cysteine |
| Q | Gln | Glutamine |
| E | Glu | Glutamic Acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |
| X | Xaa | Any amino acid as above |

TABLE 2

| Code | Non-conventional amino acid | Code | Non-conventional amino acid |
|---|---|---|---|
| Hyp | hydroxyproline | Orn | ornithine |
| Norb | aminonorbornyl-carboxylate | Abu | α-aminobutyric acid |
| Cpro | aminocyclopropane-carboxylate | Dala | D-alanine |
| Narg | N-(3-guanidinopropyl)glycine | Darg | D-arginine |
| Nasn | N-(carbamylmethyl)glycine | Dasn | D-asparagine |
| Nasp | N-(carboxymethyl)glycine | Dasp | D-aspartic acid |
| Ncys | N-(thiomethyl)glycine | Dcys | D-cysteine |
| Ngln | N-(2-carbamylethyl)glycine | Dgln | D-glutamine |
| Nglu | N-(2-carboxyethyl)glycine | Dglu | D-glutamic acid |
| Nhis | N-(imidazolylethyl)glycine | Dhis | D-histidine |
| Nile | N-(1-methylpropyl)glycine | Dile | D-isoleucine |
| Nleu | N-(2-methylpropyl)glycine | Dleu | D-leucine |
| Nlys | N-(4-aminobutyl)glycine | Dlys | D-lysine |
| Nmet | N-(2-methylthioethyl)glycine | Dmet | D-methionine |
| Norn | N-(3-aminopropyl)glycine | Dorn | D-ornithine |
| Nphe | N-benzylglycine | Dphe | D-phenylalanine |
| Nser | N-(hydroxymethyl)glycine | Dpro | D-proline |
| Nthr | N-(1-hydroxyethyl)glycine | Dser | D-serine |
| Nhtrp | N-(3-indolylethyl)glycine | Dthr | D-threonine |
| Ntyr | N-(p-hydroxyphenyl)glycine | Dtrp | D-tryptophan |
| Nval | N-(1-methylethyl)glycine | Dtyr | D-tyrosine |
| Nmgly | N-methylglycine | Dval | D-valine |
| Nmala | L-N-methylalanine | Dnmala | D-N-methylalanine |
| Nmarg | L-N-methylarginine | Dnmarg | D-N-methylarginine |
| Nmasn | L-N-methylasparagine | Dnmasn | D-N-methylasparagine |
| Nmasp | L-N-methylaspartic acid | Dnmasp | D-N-methylasparatate |
| Nmcys | L-N-methylcysteine | Dnmcys | D-N-methylcysteine |
| Nmgln | L-N-methylglutamine | Dnmgln | D-N-methylglutamine |
| Nmglu | L-N-methylglutamic acid | Dnmglu | D-N-methylglutamate |
| Nmhis | L-N-methylhistidine | Dnmhis | D-N-methylhistidine |
| Nmile | L-N-methylisolleucine | Dnmile | D-N-methylisoleucine |
| Nmleu | L-N-methylleucine | Dnmleu | D-N-methylleucine |
| Nmlys | L-N-methyllysine | Dnmlys | D-N-methyllysine |
| Nmmet | L-N-methylmethionine | Dnmmet | D-N-methylmethionine |
| Nmorn | L-N-methylornithine | Dnmorn | D-N-methylornithine |
| Nmphe | L-N-methylphenylalanine | Dnmphe | D-N-methyl-phenylalanine |
| Nmpro | L-N-methylproline | Dnmpro | D-N-methylproline |
| Nmser | L-N-methylserine | Dnmser | D-N-methylserine |
| Nmthr | L-N-methylthreonine | Dnmthr | D-N-methylthreonine |
| Nmtrp | L-N-methyltryptophan | Dnmtrp | D-N-methyltryptophan |
| Nmtyr | L-N-methyltyrosine | Dnmtyr | D-N-methyltyrosine |
| Nmval | L-N-methylvaline | Dnmval | D-N-methylvaline |
| Nmnle | L-N-methylnorleucine | Nle | L-norleucine |
| Nmnva | L-N-methylnorvaline | Nva | L-norvaline |
| Nmetg | L-N-methyl-ethylglycine | Etg | L-ethylglycine |
| Nmtbug | L-N-methyl-t-butylglycine | Tbug | L-t-butylglycine |
| Nmhphe | L-N-methyl-homophenylalanine | Hphe | L-homophenylalanine |

TABLE 2-continued

| Code | Non-conventional amino acid | Code | Non-conventional amino acid |
|---|---|---|---|
| Nmanap | N-methyl-α-naphthylalanine | Anap | α-naphthylalanine |
| Nmpen | N-methylpenicillamine | Pen | penicillamine |
| Nmgabu | N-methyl-γ-aminobutyrate | Gabu | γ-aminobutyric acid |
| Nmchexa | N-methyl-cyclohexylalanine | Chexa | cyclohexylalanine |
| Nmcpen | N-methyl-cyclopentylalanine | Cpen | cyclopentylalanine |
| Nmaabu | N-methyl-α-amino-α-methylbutyrate | Aabu | α-amino-α-methylbutyrate |
| Nmaib | N-methyl-α-aminoisobutyrate | Aib | α-aminoisobutyric acid |
| Marg | L-α-methylarginine | Dmarg | D-α-methylarginine |
| Masn | L-α-methylasparagine | Dmasn | D-α-methylasparagine |
| Masp | L-α-methylaspartate | Dmasp | D-α-methylaspartate |
| Mcys | L-α-methylcysteine | Dmcys | D-α-methylcysteine |
| Mgln | L-α-methylglutamine | Dmgln | D-α-methylglutamine |
| Mglu | L-α-methylglutamate | Dmglu | D-α-methyl glutamic acid |
| Mhis | L-α-methylhistidine | Dmhis | D-α-methylhistidine |
| Mile | L-α-methylisoleucine | Dmile | D-α-methylisoleucine |
| Mleu | L-α-methylleucine | Dmleu | D-α-methylleucine |
| Mlys | L-α-methyllysine | Dmlys | D-α-methyllysine |
| Mmet | L-α-methylmethionine | Dmmet | D-α-methylmethionine |
| Morn | L-α-methylornithine | Dmorn | D-α-methylornithine |
| Mphe | L-α-methylphenylalanine | Dmphe | D-α-methylphenylalanine |
| Mpro | L-α-methylproline | Dmpro | D-α-methylproline |
| Mser | L-α-methylserine | Dmser | D-α-methylserine |
| Mthr | L-α-methylthreonine | Dmthr | D-α-methylthreonine |
| Mtrp | L-α-methyltryptophan | Dmtrp | D-α-methyltryptophan |
| Mtyr | L-α-methyltyrosine | Dmtyr | D-α-methyltyrosine |
| Mval | L-α-methylvaline | Dmval | D-α-methylvaline |
| Mnva | L-α-methylnorvaline | Ncbut | N-cyclobutylglycine |
| Metg | L-α-methylethylglycine | Nchep | N-cycloheptylglycine |
| Mtbug | L-α-methyl-t-butylglycine | Nchex | N-cyclohexylglycine |
| Mhphe | L-α-methyl-homophenylalanine | Ncdec | N-cyclodecylglycine |
| Manap | α-methyl-α-naphthylalanine | Ncdod | N-cyclododecylglycine |
| Mpen | α-methylpenicillamine | Ncoct | N-cyclooctylglycine |
| Mgabu | α-methyl-γ-aminobutyrate | Ncpro | N-cyclopropylglycine |
| Mchexa | α-methyl-cyclohexylalanine | Ncund | N-cycloundecylglycine |
| Mcpen | α-methyl-cyclopentylalanine | Naeg | N-(2-aminoethyl)glycine |
| Nnbhm | N-(N-(2,2-diphenylethyl) carbamylmethyl-glycine | Nbhm | N-(2,2-diphenylethyl)glycine |
| Nnbhe | N-(N-(3,3-diphenylpropyl) carbamylmethyl-glycine | Nbhe | N-(3,3-diphenylpropyl)glycine |
| Tic | 1,2,3,4-tetrahydroisoquinoline-3-carboxylic acid | Nmbc | 1-carboxy-1-(2,2-diphenyl ethylamino)cyclopropane |
| pThr | phosphothreonine | pSer | phosphoserine |
|  | O-methyl-tyrosine | pTyr | phosphotyrosine |
|  | hydroxylysine |  | 2-aminoadipic acid |

The peptides of some embodiments of the invention are preferably utilized in a linear form, although it will be appreciated that in cases where cyclicization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

Further contemplated modifications of the peptides of the present invention include C-terminal amidation.

In order to improve the bioavailability of the ERK peptides, a single, a portion or even all the amino acids in the peptide can be D amino acids which are not susceptible to enzymatic proteolytic activity and can improve altogether the use of the peptides of the invention as pharmaceuticals. The peptides of the present invention may be attached (either covalently or non-covalently) to a penetrating agent.

As used herein the phrase "penetrating agent" refers to an agent which enhances translocation of any of the attached peptide across a cell membrane.

According to one embodiment, the penetrating agent is a peptide and is attached to the ERK derived peptide (either directly or non-directly) via a peptide bond. Preferably, the penetrating agent is attached to the N terminus of the ERK derived peptide.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

By way of a non-limiting example, cell penetrating peptide (CPP) sequences may be used in order to enhance intracellular penetration. CPPs may include short and long versions of the protein transduction domain (PTD) of HIV TAT protein, such as for example, YARAAARQARA (SEQ ID NO: 11), YGRKKRR (SEQ ID NO: 8), YGRKKRRQRRR (SEQ ID NO: 9), or RRQRR (SEQ ID NO: 10)]. However, the disclosure is not so limited, and any suitable penetrating agent may be used, as known by those of skill in the art.

When the peptides of the present invention are attached to cell penetrating peptides, it is contemplated that the full length peptide is no greater than 25 amino acids, no greater than 26 amino acids, no greater than 27 amino acids, no greater than 28 amino acids, no greater than 29 amino acids, or no greater than 30 amino acids.

Another method of enhancing cell penetration is via N-terminal myristoilation. In this protein modification, a myristoyl group (derived from myristic acid) is covalently attached via an amide bond to the alpha-amino group of an N-terminal amino acid of the peptide.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

As mentioned, the article of manufacture of this aspect of the present invention also comprises an ERK pathway inhibitor.

ERK pathway inhibitors refer to agents that are capable of downregulating an amount and/or activity (e.g. kinase activity) of at least one protein component of the ERK pathway in the cytoplasm of the cell. Thus for example, an ERK pathway inhibitor does not refer to an agent that prevents the translocation of ERK from the cytoplasm to the nucleus of the cell.

Such components include for example the kinases PI3K, Raf, MEK, GSK-3 and ERK. Preferably, the ERK pathway inhibitors act directly on at least one of the above mentioned components or a DNA or RNA encoding the kinases. In one embodiment, the ERK pathway inhibitor is a small molecule inhibitor which acts directly on one of PI3K, Raf, MEK, GSK-3 or ERK1/2.

According to a particular embodiment, the ERK pathway inhibitor is not a peptide.

According to a particular embodiment, the ERK pathway inhibitor is a MEK inhibitor.

As used herein, the term "MEK inhibitor" refers to a chemical or drug that inhibits the mitogen-activated protein kinase enzymes MEK1 and/or MEK2.

In one embodiment, the MEK inhibitor is a Pan-MEK inhibitor, including for example trametinib, U0126-EtOH, MEK162 or PD184352. In another embodiment, the MEK inhibitor is a selective MEK inhibitor such as Selumetinib (MEK1) or MIX 02189 (MEK5).

In another embodiment, the Raf inhibitor is a Pan-Raf inhibitor, including for example Vemurafenib, Sorafenib, LGX818 or Dabrafenib. In another embodiment, the Raf inhibitor is a selective Raf inhibitor, including for example GDC-0879 (B-Raf) or GW5074 (C-Raf).

In another embodiment, the PI3K inhibitor is a Pan-PI3K inhibitor, including for example BEZ235, GDC0941 or LY294002. In another embodiment, the PI3K inhibitor is a selective PI3K inhibitor, including for example HS-173, TGX-221, CZC24832 or CAL-101.

In another embodiment, the GSK-3 inhibitor is a Pan-GSK-3 inhibitor, including for example CHIR-99021, SB216763 or CHIR-98014. In another embodiment, the GSK-3 inhibitor is a selective GSK-3 inhibitor, including for example TWS119 or Tideglusib.

In another embodiment, the ERK inhibitor is SCH772984, XMD8-92, FR 180204 or GDC-0994.

Preferably, the article of manufacture comprises (i) a peptide agent which is capable of preventing extracellular signal-regulated kinase1/2 (ERK) translocation into the nucleus (as described herein above); and (ii) a MEK inhibitor (as described herein above).

The present invention also contemplates that the ERK pathway inhibitor is a polynucleotide agent that is capable of down-regulating expression of at least one component of the ERK pathway—e.g. PI3K, Raf, MEK, GSK-3 or ERK1/2.

As used herein the phrase "downregulates expression" refers to downregulating the expression of a protein at the genomic (e.g. homologous recombination and site specific endonucleases) and/or the transcript level using a variety of molecules which interfere with transcription and/or translation (e.g., RNA silencing agents) or on the protein level (e.g., aptamers, small molecules and inhibitory peptides, antagonists, enzymes that cleave the polypeptide, antibodies and the like).

For the same culture conditions the expression is generally expressed in comparison to the expression in a cell of the same species but not contacted with the agent or contacted with a vehicle control, also referred to as control.

Down regulation of expression may be either transient or permanent.

According to specific embodiments, down regulating expression refers to the absence of mRNA and/or protein, as detected by RT-PCR or Western blot, respectively.

According to other specific embodiments down regulating expression refers to a decrease in the level of mRNA and/or protein, as detected by RT-PCR or Western blot, respectively. The reduction may be by at least a 10%, at least 20%, at least 30%, at least 40%, at least 50%, at least 60%, at least 70%, at least 80%, at least 90%, at least 95% or at least 99% reduction.

According to specific embodiments the agent capable of downregulating a component of the ERK pathway is an antibody or antibody fragment capable of specifically binding to one of PI3K, Raf, MEK, GSK-3 or ERK1/2. Preferably, the antibody specifically binds at least one epitope of PI3K, Raf, MEK, GSK-3 or ERK1/2. As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

As PI3K, Raf, MEK, GSK-3 and ERK1/2 are localized intracellularly, the antibodies of this aspect of the present invention are typically intracellular antibodies.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Another agent which can be used along with some embodiments of the invention to downregulate a component of the ERK pathway is an aptamer. As used herein, the term "aptamer" refers to double stranded or single stranded RNA molecule that binds to specific molecular target, such as a protein. Various methods are known in the art which can be used to design protein specific aptamers. The skilled artisan can employ SELEX (Systematic Evolution of Ligands by Exponential Enrichment) for efficient selection as described in Stoltenburg R, Reinemann C, and Strehlitz B (Biomolecular engineering (2007) 24(4):381-403).

Down-Regulation at the Nucleic Acid Level

Down-regulation at the nucleic acid level is typically effected using a nucleic acid agent, having a nucleic acid backbone, DNA, RNA, mimetics thereof or a combination of same. The nucleic acid agent may be encoded from a DNA molecule or provided to the cell per se.

Thus, downregulation of a component of the ERK pathway can be achieved by RNA silencing.

As used herein, the term "RNA silencing agent" refers to an RNA which is capable of specifically inhibiting or "silencing" the expression of a target gene. In certain embodiments, the RNA silencing agent is capable of preventing complete processing (e.g. the full translation and/or expression) of an mRNA molecule through a post-transcriptional silencing mechanism.

RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433. and Diallo et al, Oligonucleotides, Oct. 1, 2003, 13(5): 381-392. doi:10.1089/154545703322617069.

According to an embodiment of the invention, the long dsRNA is specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is suggested to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include are disclosed in International Patent Application Nos. WO2013126963 and WO2014107763. It will be recognized by one of skill in the art that the resulting single chain oligonucleotide forms a stem-loop or hairpin structure comprising a double-stranded region capable of interacting with the RNAi machinery.

It will be appreciated that, and as mentioned hereinabove, the RNA silencing agent of some embodiments of the invention need not be limited to those molecules containing only RNA, but further encompasses chemically-modified nucleotides and non-nucleotides. miRNA and miRNA mimics—According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

The term "microRNA mimic" or "miRNA mimic" refers to synthetic non-coding RNAs that are capable of entering the RNAi pathway and regulating gene expression. miRNA mimics imitate the function of endogenous miRNAs and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Preparation of miRNAs mimics can be effected by any method known in the art such as chemical synthesis or recombinant methods.

It will be appreciated from the description provided herein above that contacting cells with a miRNA may be effected by transfecting the cells with e.g. the mature double stranded miRNA, the pre-miRNA or the pri-miRNA.

The pre-miRNA sequence may comprise from 45-90, 60-80 or 60-70 nucleotides.

The pri-miRNA sequence may comprise from 45-30,000, 50-25,000, 100-20,000, 1,000-1,500 or 80-100 nucleotides.

Antisense—Antisense is a single stranded RNA designed to prevent or inhibit expression of a gene by specifically hybridizing to its mRNA. Downregulation of a component of the ERK pathway can be effected using an antisense polynucleotide capable of specifically hybridizing with an mRNA transcript encoding same.

Nucleic acid agents can also operate at the DNA level as summarized infra.

Downregulation of a component of the ERK pathway can also be achieved by inactivating the gene via introducing targeted mutations involving loss-of function alterations (e.g. point mutations, deletions and insertions) in the gene structure.

As used herein, the phrase "loss-of-function alterations" refers to any mutation in the DNA sequence of a gene which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

Methods of introducing nucleic acid alterations to a gene of interest are well known in the art [see for example Menke D. Genesis (2013) 51:-618; Capecchi, Science (1989) 244: 1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDS) and non-homologous end-joining (NFfEJ). NFfEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8, 124,369; 8, 129,134; 8,133,697; 8,143,015; 8,143,016; 8, 148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www.talendesign.org). TALEN can also be designed and obtained commercially from e.g., Sangamo Biosciences™ (Richmond, Calif.).

CRISPR-Cas system—Many bacteria and archaea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337: 816-821). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvik and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec 1, (2003) 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosyltransferase (ARPT).

As mentioned, the present inventors conceive of an article of manufacture which comprise both the agent which is capable of preventing extracellular signal-regulated kinase1/2 (ERK) translocation into the nucleus and the ERK pathway inhibitor.

In one embodiment, the article of manufacture is presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

In the article of manufacture, the agent which is capable of preventing extracellular signal-regulated kinase1/2 (ERK) translocation into the nucleus may be packaged in separate packaging from the ERK pathway inhibitor. In another embodiment, the agent which is capable of preventing extracellular signal-regulated kinase1/2 (ERK) translocation into the nucleus is packaged in the same packaging as the ERK pathway inhibitor. Thus for example, the agent which is capable of preventing extracellular signal-regulated kinase1/2 (ERK) translocation into the nucleus may be formulated in the same formulation as the ERK pathway inhibitor (i.e. co-formulation).

Thus, according to another aspect of the present invention there is provided a pharmaceutical composition comprising as active agents:

(i) an agent which is capable of preventing extracellular signal-regulated kinase1/2 (ERK) translocation into the nucleus and;

(ii) an ERK pathway inhibitor (e.g. a MEK inhibitor);

and a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent which is capable of preventing extracellular signal-regulated kinase1/2 (ERK) translocation into the nucleus and the ERK pathway inhibitor accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietictissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran.

Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans. Since administration of the disclosed combination is expected to produce improved results over the administration of single agents, the therapeutically effective dose of each of the agents in the combined treatment may be for example less than 50%, 40%, 30%, 20% or even less than 10% the of the FDA approved dose.

For example, therapeutically effective dose of the ERK pathway inhibitor (e.g. MEK inhibitor) in the combined treatment may be for example less than 50%, 40%, 30%, 20% or even less than 10% the of the FDA approved dose.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The combination therapy (in the article of manufacture or pharmaceutical composition of the present invention) is useful for treating cancer.

Examples of cancers that may be treated using the combination therapy of this aspect of the present invention include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to a specific embodiment, the cancer is melanoma, breast cancer, lung cancer, prostate cancer, pancreatic cancer or cervical cancer.

In one embodiment, the cancer is resistant to ERK pathway inhibitors (e.g. BRAF or MEK inhibitor resistant cancers) when provided as a single agent.

Several resistance mechanisms have been proposed to date, which result from either preexisting mechanisms in some or all cells within the tumors or due to drug-induced mechanisms. These include i) expression of drug-resistant RAF isoforms ii) molecular or genetic alterations of downstream components that reactivate the ERK cascade and iii) induction of upstream components and other signaling pathways that bypass the drug blockage. All these mechanisms eventually result in inducing reactivation of ERK or other survival-related pathways.

Alternatively, the cancer which is treated has not been previously treated with an ERK pathway inhibitor (e.g. a BRAF inhibitor) in the absence of the peptide. Thus, it is envisaged that the first line treatment of the cancer is the combination of the ERK pathway inhibitor and the peptide. In one embodiment, the cancer is non-resistant to the effects of the ERK pathway inhibitor. In another embodiment, the cancer is resistant to the effect of the ERK pathway inhibitor (when used as a sole treatment).

According to another embodiment, the melanoma is BRAF mutant melanomas, a NRAS mutant melanoma and a NF1 mutant melanoma.

The NRAS mutant melanoma may comprise at least one mutation selected from the group consisting of 63T, 83T, 120T and 60T.

The NF1 mutant melanoma comprises at least one mutation as set forth in Table 3 of the Examples section herein below.

In the context of a combination therapy, the ERK pathway inhibitors may be administered by the same route of administration (e.g. intrapulmonary, oral, enteral, etc.) as the agents which prevent ERK nuclear translocation are administered. In the alternative, the ERK pathway inhibitors may be administered by a different route of administration to the agents which prevent ERK nuclear translocation.

The ERK pathway inhibitors can be administered immediately prior to (or after) the agents which prevent ERK nuclear translocation, on the same day as, one day before (or after), one week before (or after), one month before (or after), or two months before (or after) the agents which prevent ERK nuclear translocation, and the like.

The ERK pathway inhibitors and the agents which prevent ERK nuclear translocation can be administered concomitantly, that is, where the administering for each of these reagents can occur at time intervals that partially or fully overlap each other. The ERK pathway inhibitors and the agents which prevent ERK nuclear translocation can be administered during time intervals that do not overlap each other. For example, the ERK pathway inhibitors can be administered within the time frame of t=0 to 1 hours, while the agents which prevent ERK nuclear translocation can be administered within the time frame of t=1 to 2 hours. Also, the ERK pathway inhibitors can be administered within the time frame of t=0 to 1 hours, while the agents which prevent ERK nuclear translocation can be administered somewhere within the time frame of t=2-3 hours, t=3-4 hours, t=4-5 hours, t=5-6 hours, t=6-7 hours, t=7-8 hours, t=8-9 hours, t=9-10 hours, and the like. Moreover, the agents which prevent ERK nuclear translocation can be administered somewhere in the time frame of t=minus 2-3 hours, t=minus 3-4 hours, t=minus 4-5 hours, t=5-6 minus hours, t=minus 6-7 hours, t=minus 7-8 hours, t=minus 8-9 hours, t=minus 9-10 hours.

The agents which prevent ERK nuclear translocation of the present invention and the ERK pathway inhibitors are typically provided in combined amounts to achieve therapeutic, prophylactic and/or pain palliative effectiveness. This amount will evidently depend upon the particular compound selected for use, the nature and number of the other treatment modality, the condition(s) to be treated, prevented and/or palliated, the species, age, sex, weight, health and prognosis of the subject, the mode of administration, effectiveness of targeting, residence time, mode of clearance, type and severity of side effects of the pharmaceutical composition and upon many other factors which will be evident to those of skill in the art. The agents which prevent ERK nuclear translocation will be used at a level at which therapeutic, prophylactic and/or pain palliating effectiveness in combination with the ERK pathway inhibitors will be observed.

The ERK pathway inhibitors may be administered at a gold standard dosing as a single agent, below a gold standard dosing as a single agent or above a gold standard dosing as a single agent.

According to specific embodiments, the ERK pathway inhibitor is administered below gold standard dosing as a single agent.

As used herein the term "gold standard dosing" refers to the dosing which is recommended by a regulatory agency (e.g., FDA), for a given tumor at a given stage.

According to other specific embodiments the ERK pathway inhibitor is administered at a dose that does not exert at least one side effect which is associated with the gold standard dosing. Non-limiting examples of side effects of a ERK pathway inhibitor treatment include skin rash, diarrhea, mouth sores, paronychia, fatigue, hyperglycemia, hepatotoxicity, kidney failure, cardiovascular effects, electrolytes anomalies and GI perforations.

Thus, in one preferred embodiment, the amount of the ERK pathway inhibitor is below the minimum dose required for therapeutic, prophylactic and/or pain palliative effectiveness when used as a single therapy (e.g. 10-99%, preferably 25 to 75% of that minimum dose). This allows for reduction of the side effects caused by the ERK pathway inhibitor but the therapy is rendered effective because in combination with the agent which prevents ERK nuclear translocation, the combinations are effective overall.

In one preferred aspect of the present invention, the agent which prevents ERK nuclear translocation and the ERK pathway inhibitor are synergistic with respect to their dosages. That is to say that the effect provided by the compound of the present invention is greater than would be anticipated from the additive effects of the ERK pathway inhibitor and the agent which prevents ERK nuclear translocation when used separately. In an alternative but equally preferred embodiment, the ERK pathway inhibitor of the present invention and the agent which prevents ERK nuclear translocation are synergistic with respect to their side effects. That is to say that the side-effects caused by the agents which prevent ERK nuclear translocation in combination with the ERK pathway inhibitor are less than would be anticipated when the equivalent therapeutic effect is provided by either the ERK pathway inhibitor or by the agent which prevents ERK nuclear translocation when used separately.

It will be appreciated that as well as combination therapy, the present inventors also contemplate treating NRAS mutant melanoma and an NF1 mutant melanoma with peptides that prevents ERK nuclear translocation.

Thus, according to still another aspect of the present invention there is provided a method of treating NRAS mutant melanoma and an NF1 mutant melanoma, the method comprising administering to the subject a therapeutically effective amount of a peptide which comprises the sequence $X_1 X_2 X_3$ (SEQ ID NO: 12) wherein:

(i) $X_1$ and $X_3$ are each independently selected from the group consisting of serine, phosphoserine, threonine, phosphothreonine, aspartic acid and glutamic acid;

(ii) $X_2$ is proline; and (iii) the peptide is no longer than 30 amino acids.

Examples of peptides that can be used as single therapy are detailed herein above.

According to a specific embodiment, the peptide comprises the sequence as set forth in SEQ ID NO: 2.

It is expected that during the life of a patent maturing from this application many relevant ERK pathway inhibitors and agents which prevent ERK nuclear translocation will be developed and the scope of the term ERK pathway inhibitors is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Reagents: Tetradecanoyl phorbol acetate (TPA), poly-L-Lysine (PLL) and 4,6-diamino-2-phenylindole (DAPI) were purchased from Sigma-Aldrich (Rehovot, Israel). Albumin bovine serum (BSA) was purchased from MP biomedical (OH, USA). The BRAF inhibitor PLX4032 and MEK inhibitor Trametinib (GSK1120212) were purchased from SelleckChem (Huston, Tex.). CellTiter-Glo reagent was purchased from Promega (Madison, Wis.).

Buffers: Sample buffer 2X: 2.5% SDS, 25% glycerol, 125 mM Tris Cl ph 6.8, 4% v/v β-mercaptoethanol. 0.01% bromophenol blue. TBST wash buffer: 200 mM Tris (pH 7.5), 1.5 M NaCl, 0.5% Tween 20.

Antibodies: Anti-phosphorylated Elk1 (B-4, S383; pElk1, 1:1000), general RSK1 (C-21; 1:4000), pRSK1/2 (T359, S381; 1:2000), p-cMyc (T58, S62; 1:1000) and GAPDH (FL-335; 1:1000) antibodies (Abs) were obtained from Santa Cruz Biotechnology (CA, USA). Anti-CyclinD1 (92G2, 1:1000) and PARP (46D11, 1:1000) Abs were obtained from Cell Signaling Technology (Beverly, Mass., USA). Anti-pERK1/2 (1:20000) and gERK1/2 (1:20000) Abs were obtained from Sigma (Rehovot, Israel). Anti-Sprouty2 (aminoterminal, 1:1000) Ab was obtained from Abcam (Cambridge, UK). Secondary fluorescent Ab conjugates were obtained from Jackson ImmunoResearch (West Grove, Pa.). Secondary Abs conjugated to horseradish peroxidase (HRP) were obtained from Nichirei Biosciences (Japan).

Peptides: The peptides used were: Scrambled (Scr), GNILSQELPHSGDLQIGL (SEQ ID NO; 1), and EPE: GQLNHILGILGEPEQEDL) (SEQ ID NO: 2). Both peptides were N-terminal conjugated to myristic acid[53] and C-terminal amidated, purchased from GenScript (HGK, China), purity >85% and kept as 100 mM in DMSO at −20° C.

Cells: Low-passage primary melanoma cells A2352 were from the Ella Institute, Sheba Medical Center, Israel. Established melanoma cell A375 was from ATCC.

Tumor Tissue: A subset of cell lines used in the study ('T' cells) were derived from a panel of pathology-confirmed metastatic melanoma tumor resections collected from patients enrolled in institutional review board (IRB)-approved clinical trials at the Surgery Branch of the National Cancer Institute. These cell lines were established at the NCI with informed patient consent under on a clinical protocol (03-C-0277) approved by the institutional-review board (IRB) of the National Cancer Institute (NCI). Pathology-confirmed melanoma cell lines were derived from mechanically or enzymatically dispersed tumor cells, which were then cultured in RPMI-1640 supplemented with 10% FBS at 37° C. in 5% CO2 for 5-15 passages. Cell line genotypes are given in Table 3. All cell lines have tested negative for mycoplasma.

PCR sequencing and mutational analysis: PCR and sequencing of BRAF, NRAS and NF1 were carried out as described in Palavalli, L. H. et al. Nat Genet 41, 518-520, doi:10.1038/ng.340 (2009); and Arafeh, R. et al. Nat Genet 47, 1408-1410, doi:10.1038/ng.3427 (2015).

Fluorescence microscopy: Cells were seeded on coverslips coated with 0.001% w/v poly-L-Lysine (PLL) at 60% confluency. After treatments, cells were fixed in 4% paraformaldehyde/PBS$^{-/-}$ for 20 min on ice surface, permeabilized with 0.1% Triton X-100/PBS$^{-/-}$ for 5 min at 23° C., then blocked in 2% BSA/PBS$^{-/-}$ for 30 min at 23° C. The fixed cells were sequentially incubated with appropriate Abs, (in 2% BSA/PBS, 1.5 h), washed 3 times with PBS$^{-/-}$, and followed by incubation with either Cy-2 or rhodamine-conjugated secondary Abs (1:200) and DAPI (1:100) in 2% BSA/PBS$^{-/-}$ for 1 h. Slides were analyzed and photographed by a fluorescence microscope (Olympus BX51, x40). Background correction, and contrast adjustment of raw data images were performed using Photoshop (Adobe, Calif., USA).

Preparation of cellular extracts and Western blotting: Cells were grown to 70% confluence and serum starved (0.1% FCS, 16 h). After treatments, cell media was collected and floating cells where pelleted (8000 rpm, 1 min, 4° C.) and lysed in sample buffer 2x. In parallel, adherent cells were scraped into sample buffer 2x and combined with pelleted cells. The extracts were sonicated (50 W, 2×7 s), incubated on ice for 15 min, and boiled for 5 min. The samples were then subjected to 10% SDS-PAGE and Western blotting with the appropriate Abs. The blots were developed with HRP-conjugated anti-mouse or anti-rabbit Abs, using SuperSignal West Pico Chemiluminescent Substrate™ from Thermo Scientific (Waltham, Mass., USA). Quantification of blots was done using ImageJ.

Cell viability assay: Cells were seeded at a density of 4000 cells per well into 96-well plates in complete medium. After 24 h, medium was replaced by 1% FCS containing appropriate treatments. Fresh medium containing the same agents was replaced every day. After 96 h, cell proliferation was assessed using the CellTiter-Glo reagent (Promega). $IC_{50}$ values were determined using GraphPad Prism.

Results

Effect of Inhibition of Nuclear ERK1/2 Translocation by the EPE Peptide on the Viability of Metastatic Melanoma Cells The EPE peptide has been shown to inhibit the proliferation of several cancer cell types, and induces apoptosis in BRAF melanomas, while other types of melanoma were only partially affected [Plotnikov, A. et al. Nat Commun 6, 6685, doi:10.1038/ncomms7685 (2015)]. In this current study, the present inventors extended the screen to include melanoma cells with a variety of mutational backgrounds, in order to assess the effect of the EPE peptide on the viability of melanoma cells. They selected 36 melanoma cell lines, corresponding to the three major groups of mutations in melanoma: BRAF mutant, NRAS mutant, and NF1 mutant melanomas as set forth in Table 3 herein below, and evaluated their sensitivity to the EPE peptide according to the percentage of viability of EPE-treated cells compared to Scrambled (Scr) peptide control: Sensitive (below 60%), partial response (60%-80%) and resistant (above 80%) (FIGS. 11A-B).

TABLE 3

BRAF, NRAS and NF1 mutations in different melanomas cell lines. WT: Wild-Type, N/A: Not Available

| Cell line | BRAF | NRAS | NF1 |
| --- | --- | --- | --- |
| A375 | V600E | WT | WT |
| A2352 | V600E | WT | N/A |
| Mel Juso | WT | Q61L | L1779 |

TABLE 3-continued

BRAF, NRAS and NF1 mutations in different melanomas cell lines. WT: Wild-Type, N/A: Not Available

| Cell line | BRAF | NRAS | NF1 |
|---|---|---|---|
| 2T | D594G | Q61K | WT |
| 5T | V600E | WT | WT |
| 10T | V600E | WT | N/A |
| 13T | WT | WT | P1084S |
| 17T | WT | Q61K | WT |
| 20T | V600E | WT | N/A |
| 26T | V600E | WT | WT |
| 29T | V600E | WT | N/A |
| 30T | V600E | WT | N/A |
| 32T | L597Q, P367L | WT | L628F |
| 38T | V600E | WT | N/A |
| 39T | WT | WT | S404F, Q1174 * |
| 44T | WT | Q61K | N/A |
| 45T | V600E | WT | E1320K |
| 48T | V600E | WT | N/A |
| 51T | V600E | WT | WT |
| 60T | WT | Q61R | WT |
| 63T | WT | Q61K | R530K |
| 74T | WT | Q61R | N/A |
| 76T | WT | WT | P1667S, R1613Q |
| 83T | V600E | G13R | WT |
| 85T | V600E | WT | N/A |
| 88T | V600E | WT | WT |
| 99T | V600E | WT | N/A |
| 100T | V600E | WT | N/A |
| 101T | L594V | Q61K | N/A |
| 103T | V600E | WT | N/A |
| 104T | WT | G13R | N/A |
| 108T | WT | WT | H1366Q |
| 110T | WT | Q61K | N/A |
| 112T | WT | Q61R | N/A |
| 116T | WT | Q61R | N/A |
| 120T | WT | Q61L | N/A |

Figure 1B:
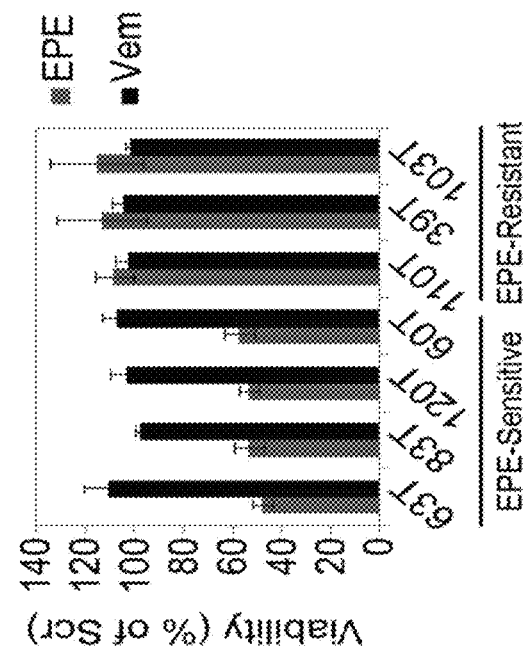
FIGS. 1A-B: The EPE peptide reduces viability of BRAF, NRAS and NF1 mutant melanoma cell lines. (A) Effect of the EPE peptide on proliferation of metastatic melanoma cells. Thirty-six melanoma cell lines derived from metastatic tumor resections were treated with either EPE or scrambled (Scr) peptides (10 μM). A subset of BRAF, NRAS and NF1 mutant melanomas were sensitive to the EPE peptide. Bars in white correspond to cell lines selected for further study. (B) Effect of BRAF inhibitor vemurafenib on selected melanomas. Four EPE-sensitive NRAS melanomas (63T, 83T, 120T and 60T), and three EPE-resistant melanomas (110T, 39T, 103T) were treated either with vemurafenib (1 μM, Vem), EPE or Scr peptide (10 μM). All melanoma cells selected were resistant to BRAF inhibition. Cell viability was measured by CellTiter-Glo reagent after 72 h of treatment. Bars represent percentage of growth respect to Scr peptide control ±S.E. of 3 independent experiments.
Figure 1A:
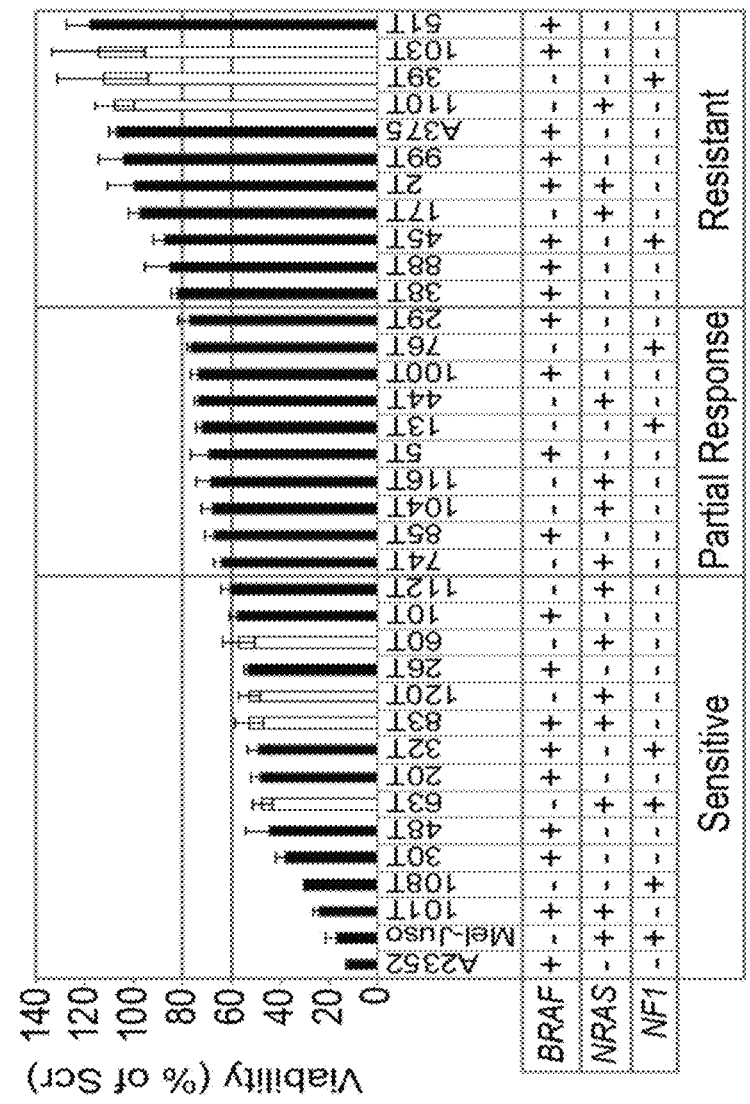

Interestingly, it was found that the EPE peptide was effective not only in reducing the viability of BRAF mutant melanomas, but it also affected cell lines bearing NRAS and/or NF1 mutations as well. Some NRAS and BRAF mutant melanomas were sensitive to the EPE peptide, while others were either partially sensitive or not sensitive at all. Some of the NF1 melanoma cells tested were very sensitive to the peptide, but others were either partially responsive or did not respond to the EPE peptide. Unexpectedly, more NRAS melanomas, that are less sensitive to clinical RAF and MEK inhibitors [Kelleher, F. C. & McArthur, G. A. Cancer J 18, 132-136, doi:10.1097/PPO.0b013e31824ba4df (2012)], were found in the sensitive group compared to other groups. These results indicate that the EPE peptide affects the pERK-addicted melanomas, but likely requires some additional aberrations to exert its effects. Since NRAS mutant melanomas lack an effective targeted therapy, the present inventors decided to continue their studies with four NRAS melanoma cell lines that were sensitive to EPE peptide (63T, 83T, 120T and 60T). In addition, they selected three EPE-resistant cell lines with diverse mutational backgrounds (110T—NRAS mutant; 39T—NF1 mutant; and 103T—BRAF mutant) to shed light on the mechanism of resistance to EPE treatment (FIG. 1A, white bars). All EPE-sensitive NRAS melanomas selected were resistant to the BRAF inhibitor vemurafenib, while the EPE peptide reduced their viability to 50%. Importantly, all three EPE-resistant melanomas selected were also resistant to BRAF inhibition (FIG. 1B), indicating a common ERK related mechanism of resistance.

Effect of the EPE Peptide on Nuclear ERK1/2 Translocation and Activity

In order to better understand the differences between EPE sensitive and resistant melanoma cells, the present inventors decided to examine whether there are differences in the ability of the EPE peptide to block the nuclear translocation of ERK1/2 in the different cells. In resting cells, ERK1/2 was predominantly localized in the cytosol (white bars) in six of the seven cell lines (FIGS. 2A-B). After 15 minutes of TPA stimulation, all cell lines underwent ERK1/2 translocation to the nucleus. In some cell lines ERK1/2 localization was mainly in the nucleus (red bars), or in some cases, presented an 'all over' distribution (equal nuclear and cytoplasmic localization) (black bars). Thus, the EPE peptide disrupted the normal stimuli-dependent nuclear translocation of ERK1/2 in all cases, but the extent of reduction on nuclear ERK1/2 localization (red bars) was much higher in sensitive cell lines (FIG. 2A), compared to resistant cells (FIG. 2B).

The present inventors next examined the effects of EPE peptide on ERK1/2 signaling. The EPE peptide did not inhibit the activity of ERK1/2 as seen by the preservation of phosphorylation of the ERK1/2's activatory TEY motif and its substrate RSK in all cell lines examined (FIG. 3A, B). In two of the sensitive cell lines, the EPE peptide reduced the phosphorylation of the nuclear targets Elk1 and c-Myc in basal and stimulated state. However, in EPE resistant cells, the peptide slightly increased the phosphorylation levels of c-Myc and had no effect on the phosphorylation of Elk1 (FIG. 3B). These results may suggest that a small amount of the EPE peptide can enter the cells, but these amounts have a small effect on the signaling of resistant cells. Therefore, the mechanism of EPE peptide resistance is most likely not related to faster degradation or an impediment of the peptide to enter the cells. Given that the EPE peptide slightly affects the nuclear translocation of ERK1/2 and the levels of P-c-Myc in resistant cells, it is likely that the resistance is caused by the small amount of peptide, although other mechanisms may be involved as well.

Synergistic Effect of Trametinib and EPE Peptide Combination in Reducing the Viability of Melanoma Cells Although the response rates to treatment with BRAF inhibitor vemurafenib can reach 60-80% in BRAFV$^{600}$E melanoma patients, only a few patients achieve single-agent complete response. This is mainly due to a relatively rapid development of resistance to ERK cascade inhibitors. In most cases, patients who had a positive initial response to single treatment with ERK cascade inhibitors, eventually relapse and develop resistance within months to a year by accumulating additional driver mutations in their tumors or by finding other escape routes that usually reactivate the ERK cascade. Use of drug combinations have the potential to address these different resistance mechanisms. The present inventors therefore tested whether combining the MEK inhibitor trametinib and the ERK1/2 nuclear translocation inhibitor EPE peptide, could overcome the drug resistance (or lack of response) that metastatic melanoma cells showed when treated with each drug individually.

Figure 5:
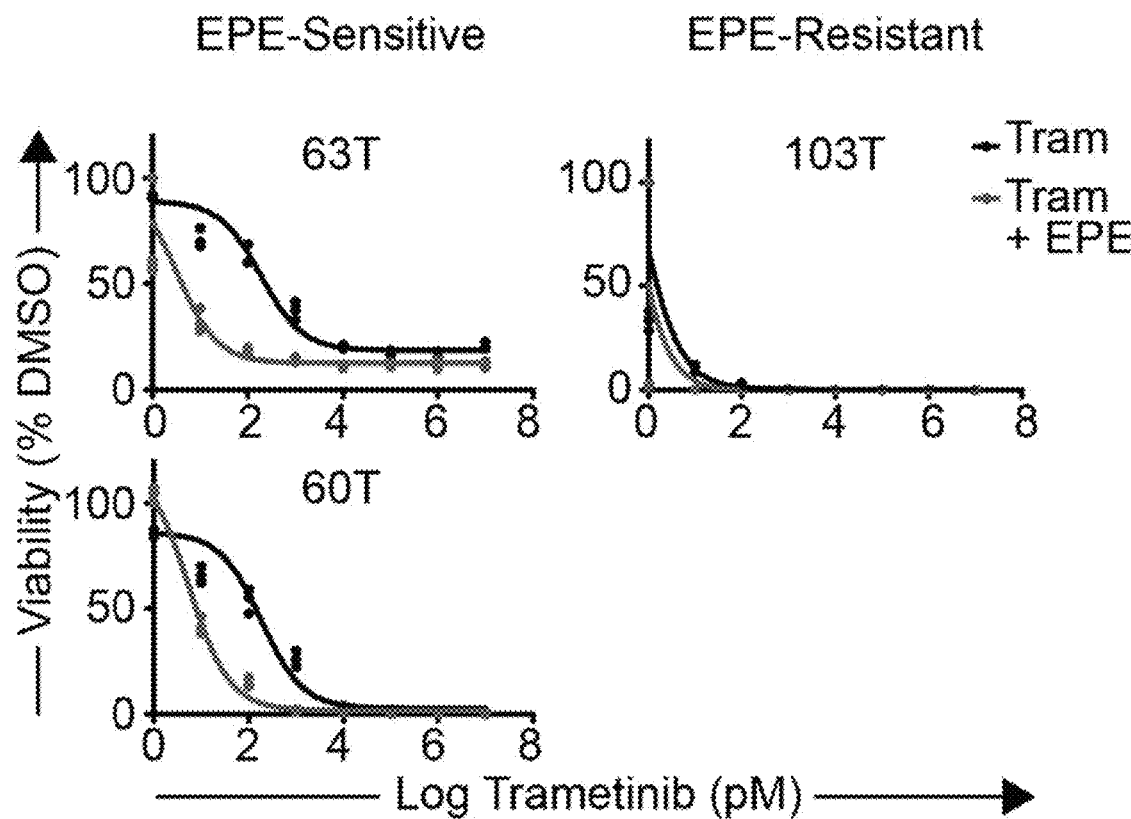
FIG. 5: Synergistic effect of trametinib and EPE peptide combination in reducing the viability of melanoma cell lines. Synergy between combined treatment of trametinib and EPE peptide in patient-derived melanoma cells. Dose response curves showing growth of melanoma cells treated with combination of trametinib and EPE peptide 10 µM (red), compared to trametinib treatment alone (black). Dots represent triplicates for every concentration point.

They observed a strong synergistic effect when combining trametinib and EPE peptide in all selected melanoma cell lines, including the EPE- and vemurafenib-resistant melanoma cells ($p<0.01$, $p<0.001$, FIG. 4A, B). The IC$_{50}$ values of the combined treatment of trametinib and EPE peptide were close to 1 µM for the EPE-sensitive NRAS melanomas 83T and 120T, close to 10 µM for 110T and 1 nM for 39T (EPE-resistant melanomas). A similar trend was observed in the other cell lines (FIG. 5) Therefore, the $IC_{50}$ values for the combined treatment were two orders of magnitude lower, compared to trametinib alone, for all cell lines tested.

In order to shed light on the mechanism that drives the synergistic effect, the effect of the trametinib and EPE peptide combination on ERK cascade signaling in the EPE-sensitive 83T cells was observed. Combination of both inhibitors resulted in a more profound decrease in the phosphorylation of ERK1/2 nuclear target cMyc, but had no significant difference on the phosphorylation of cytosolic target RSK and ERK-induced expression of Cyclin D1, compared to trametinib alone (FIG. 4C). Interestingly, the levels of the activatory TEY phosphorylation motif of ERK1/2 (pERK1/2) were slightly increased in the combination treatment. This effect might be a result of a higher number of ERK1/2 molecules in the cytoplasm, which makes them more prone to phosphorylation by MEK1/2, which is only partially inhibited by very low concentration of trametinib. Consistent with the synergy effect previously observed, combination of the inhibitors resulted in increased levels of cleaved PARP, a marker of apoptosis. Most importantly, combined treatment of EPE peptide and trametinib at very low concentrations, not only preserved, but also increased the transcription-dependent Sprouty2-mediated negative feedback loop of the ERK cascade. This effect on Sprouty2 was not observed when trametinib was administered alone, or when it was combined with EPE peptide at higher combinations (FIG. 4C). This effect was unexpected, as it was initially thought that the EPE peptide does not affect the transcriptionally-induced negative feedback loops. Therefore, the results here indicate that the EPE peptide not only affects the cytosolic feedback loops but also some nuclear ones, possibly by inducing additional signaling. For example, this effect may include the EPE-dependent higher activation of RSK in the cytoplasm that later translocates into the nucleus to induce additional transcription, that is not directly affected by ERK1/2.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition comprising as active agents:
   (i) a peptide which is capable of preventing extracellular signal-regulated kinase1/2 (ERK) translocation into the nucleus, said peptide comprising a sequence selected from the group consisting of SEQ ID NO: 2, SEQ ID NO: 3 and SEQ ID NO: 6; and
   (ii) a MEK inhibitor;
   and a pharmaceutically acceptable carrier.

2. The pharmaceutical composition of claim 1, wherein said MEK inhibitor is selected from the group consisting of trametinib, selumetinib and MEK162.

3. The pharmaceutical composition of claim 1, wherein the peptide comprises a cell penetrating agent.

4. The pharmaceutical composition of matter of claim 3, wherein said cell penetrating agent is a cell penetrating peptide.

5. A method of treating pancreatic cancer or melanoma in a subject in need thereof comprising administering to the subject a therapeutically effective amount of the pharmaceutical composition of claim 1, thereby treating the pancreatic cancer or melanoma.

6. The method of claim 5, wherein said melanoma is a BRAF mutant melanoma, a NRAS mutant melanoma or a NF1 mutant melanoma.

* * * * *